(12) United States Patent
Debain et al.

(10) Patent No.: US 12,268,771 B2
(45) Date of Patent: Apr. 8, 2025

(54) COMPOSITION COMPRISING AT LEAST ONE AMINO SILICONE, AT LEAST ONE NON-AMINO SILICONE AND AT LEAST ONE COLOURING AGENT

(71) Applicant: L'OREAL, Paris (FR)

(72) Inventors: Jean-Daniel Debain, Saint Ouen (FR); Alexis Liard, Saint Ouen (FR)

(73) Assignee: L'OREAL, Paris (FR)

( * ) Notice: Subject to any disclaimer, the term of this patent is extended or adjusted under 35 U.S.C. 154(b) by 100 days.

(21) Appl. No.: 18/018,335

(22) PCT Filed: Jul. 28, 2021

(86) PCT No.: PCT/EP2021/071172
§ 371 (c)(1),
(2) Date: Jan. 27, 2023

(87) PCT Pub. No.: WO2022/023426
PCT Pub. Date: Feb. 3, 2022

(65) Prior Publication Data
US 2023/0285269 A1    Sep. 14, 2023

(30) Foreign Application Priority Data
Jul. 30, 2020  (FR) .................................... 2008121

(51) Int. Cl.
| | | |
|---|---|---|
| A61Q 5/10 | (2006.01) | |
| A61K 8/893 | (2006.01) | |
| A61K 8/898 | (2006.01) | |
| A61Q 5/06 | (2006.01) | |

(52) U.S. Cl.
CPC .............. *A61K 8/898* (2013.01); *A61K 8/893* (2013.01); *A61Q 5/065* (2013.01); *A61K 2800/43* (2013.01); *A61K 2800/594* (2013.01)

(58) Field of Classification Search
CPC .... A61K 8/898; A61K 8/893; A61K 2800/43; A61K 2800/594; A61K 8/891; A61K 8/29; A61Q 5/065
USPC .......................................................... 8/405
See application file for complete search history.

(56) References Cited

U.S. PATENT DOCUMENTS

| | | |
|---|---|---|
| 4,578,266 A | 3/1986 | Tietjen et al. |
| 5,110,318 A | 5/1992 | Altobelli et al. |
| 5,645,609 A | 7/1997 | Andrean et al. |
| 5,708,151 A | 1/1998 | Möckli |
| 11,007,131 B2 | 5/2021 | Guerin et al. |
| 2013/0129648 A1 * | 5/2013 | Nguyen ................... A61Q 5/12 424/59 |
| 2016/0166479 A1 | 6/2016 | Chiou et al. |
| 2018/0200178 A1 | 7/2018 | Colaco et al. |
| 2020/0170919 A1 | 6/2020 | Seneca et al. |

FOREIGN PATENT DOCUMENTS

| | | |
|---|---|---|
| EP | 0714954 A2 | 6/1996 |
| EP | 1184426 A2 | 3/2002 |
| EP | 1935398 A1 | 6/2008 |
| FR | 2679771 A1 | 2/1993 |
| FR | 2910297 A1 | 6/2008 |
| FR | 2936414 A1 | 4/2010 |
| FR | 3045346 A1 | 6/2017 |
| FR | 3068247 A1 | 1/2019 |
| GB | 2186890 A | 8/1987 |
| JP | 05-017710 A | 1/1993 |
| JP | 07-258460 A | 10/1995 |
| JP | 09-188830 A | 7/1997 |
| JP | 10-158450 A | 6/1998 |
| JP | 10-158451 A | 6/1998 |
| WO | 95/01772 A1 | 1/1995 |
| WO | 95/15144 A1 | 6/1995 |
| WO | WO 2020260273 A1 * | 12/2020 ............. A61Q 5/065 |

OTHER PUBLICATIONS

STIC Search Report dated Jun. 12, 2024.*
Schlossman, Mitchell L., "Treated Pigments New Ways to Impart Color on the Skin," Cosmetics and Toiletries, vol. 105, Feb. 1990, pp. 53-64.
Mintel: "Color Refresher Treatment," Schwarzkopf & Henkel, Record ID 3704135, XP55800025, Jan. 2016.
Mintel: "Color Treatment Paint," SNP Cosmetic, Record ID 7433663, XP55800021, Mar. 2020.
Mintel: "Glam Hippie 1-Day Colour Hair Makeup Kit," L'Oréal, Record ID 7058397, XP 55799564, Nov. 2019.
Mintel: "Temporary Hair Highlights," Watsons Personal Care Stores, Record ID 3629555, XP5579909, Feb. 2016.
International Search Report for counterpart Application No. PCT/EP2021/071172, dated Nov. 5, 2021.

\* cited by examiner

*Primary Examiner* — Eisa B Elhilo
(74) *Attorney, Agent, or Firm* — THE MARBURY LAW GROUP, PLLC

(57) ABSTRACT

The present invention relates to a composition for treating keratin fibres, in particular the hair, comprising: a) at least one amino silicone; b) at least one non-amino silicone having a weight-average molecular weight of less than or equal to 1500 g/mol; c) at least one colouring agent chosen from pigments, direct dyes and mixtures thereof.

19 Claims, No Drawings

COMPOSITION COMPRISING AT LEAST ONE AMINO SILICONE, AT LEAST ONE NON-AMINO SILICONE AND AT LEAST ONE COLOURING AGENT

CROSS REFERENCE TO RELATED APPLICATIONS

This is a National Stage Application of PCT/EP2021/071172, filed internationally on Jul. 28, 2021, which claims priority to Application No. FR 2008121, filed Jul. 30, 2020, both of which are incorporated by reference herein in their entireties.

A subject of the present invention is a composition for treating keratin fibres such as the hair, comprising at least one amino silicone, at least one non-amino silicone having a weight-average molecular weight of less than or equal to 1500 g/mol and at least one colouring agent chosen from pigments, direct dyes and mixtures thereof.

The present invention also relates to a process for the cosmetic treatment of, in particular for dyeing, keratin fibres such as the hair, in which the composition as described above is applied to said fibres.

Another subject of the present invention is the use of the composition according to the invention for the cosmetic treatment of keratin fibres such as the hair.

In the field of dyeing keratin fibres, in particular human keratin fibres, it is already known practice to dye keratin fibres via various techniques using direct dyes or pigments for non-permanent dyeing, or dye precursors for permanent dyeing.

There are essentially three types of process for dyeing the hair:
  a) "permanent" dyeing, the function of which is to afford a substantial modification to the natural colour and which employs oxidation dyes which penetrate into the hair fibre and forms the dye via an oxidative condensation process;
  b) non-permanent, semi-permanent or direct dyeing, which does not use the oxidative condensation process and withstands four or five shampoo washes; it consists in dyeing keratin fibres with dye compositions containing direct dyes;
  c) temporary dyeing, which gives rise to a modification of the natural colour of the hair that remains from one shampoo wash to the next, and which serves to enhance or correct a shade that has already been obtained. It may also be likened to a "makeup" process.

For this last type of dyeing, it is known practice to use coloured polymers formed by grafting one or more dyes of azo, triphenylmethane, azine, indoamine or anthraquinone nature onto a polymer chain. These coloured polymers are not entirely satisfactory, notably as regards the homogeneity of the colouring obtained and its resistance, not to mention the problems associated with their manufacture and notably with their reproducibility.

Another dyeing method consists in using pigments. Specifically, the use of pigment on the surface of keratin fibres generally makes it possible to obtain visible colourings on dark hair, since the surface pigment masks the natural colour of the fibre. However, the colourings obtained via this dyeing method have the drawback of having poor resistance to shampoo washing and also to external agents such as sebum, perspiration, blow-drying and/or rubbing.

In addition, compositions for temporarily dyeing the hair may also lead to a hair feel that is uncosmetic and/or not natural; the hair thus dyed may notably lack softness and/or suppleness and/or strand separation.

Therefore, there remains a need for a composition for treating keratin fibres, notably the hair, which has the advantage of obtaining a homogeneous and smooth coloured coating on the hair, and also hair with complete strand separation, while at the same time forming a coating that is persistent with respect to shampoo washing and to the various attacking factors to which the hair may be subjected, such as blow-drying and/or rubbing, without degrading the hair.

Thus, the aim of the present invention is to develop a composition for treating keratin fibres, notably the hair, which has the advantage of obtaining a homogeneous and smooth coloured coating on the hair, and also hair with complete strand separation, while at the same time forming a coating that is persistent with respect to shampoo washing and to the various attacking factors to which the hair may be subjected, such as blow-drying and/or rubbing, without degrading the hair.

The present invention relates to a composition for treating keratin fibres, in particular the hair, comprising:
  a) at least one amino silicone;
  b) at least one non-amino silicone having a weight-average molecular weight of less than or equal to 1500 g/mol;
  c) at least one colouring agent chosen from pigments, direct dyes and mixtures thereof.

The present invention also relates to a process for the cosmetic treatment of, in particular for dyeing, keratin fibres such as the hair, in which the composition as described above is applied to said fibres.

The present invention also relates to the use of the composition according to the invention for the cosmetic treatment of, in particular for dyeing, keratin fibres such as the hair.

By virtue of the composition according to the invention, coloured coatings are obtained on the hair that make it possible to obtain a colouring that is visible on all types of hair in a manner that is persistent with respect to shampoo washing, while at the same time preserving the physical qualities of the keratin fibres. Such a coating may be resistant to the external attacking factors to which the hair may be subjected, such as blow-drying and perspiration. It makes it possible in particular to obtain a smooth and uniform deposit.

Moreover, the composition according to the invention leaves the hair with complete strand separation, which can be styled without any problem. The hair after treatment with the composition according to the invention can be subjected to shaping treatments, preferably temporary shaping treatments.

For the purposes of the present invention, the term "hair with strand separation" means hair which, after application of the composition and drying, is not stuck together (or of which all the strands are separated from each other) and thus does not form clumps of hair.

For the purposes of the present invention, "colouring which is persistent with regard to shampooing operations" is understood to mean that the colouring obtained persists after one shampooing operation, preferably after three shampooing operations, more preferentially after five shampooing operations.

The expression "at least one" means one or more.

The invention is not limited to the examples illustrated. The features of the various examples may in particular be combined within variants which are not illustrated.

For the purposes of the present invention and unless otherwise indicated, an "alkyl" radical denotes a linear or branched saturated radical containing, for example, from 1 to 20 carbon atoms;

an "aminoalkyl" radical denotes an alkyl radical as defined previously, said alkyl radical comprising an $NH_2$ group;

a "hydroxyalkyl" radical denotes an alkyl radical as defined previously, said alkyl radical comprising an OH group;

an "alkylene" radical denotes a linear or branched divalent saturated $C_2$-$C_4$ hydrocarbon-based group such as methylene, ethylene or propylene;

a "cycloalkyl" radical denotes a saturated cyclic hydrocarbon-based group comprising from 1 to 3 rings, preferably 2 rings, and comprising from 3 to 20 carbon atoms, preferably between 5 and 10 carbon atoms, such as cyclopentyl, cyclohexyl, cycloheptyl, norbornyl, or isobornyl, the cycloalkyl radical possibly being substituted with one or more ($C_1$-$C_4$)alkyl groups such as methyl;

an "aryl" radical is a cyclic unsaturated aromatic radical comprising from 6 to 12 carbon atoms, which is mono- or bicyclic, fused or unfused; preferably, the aryl group comprises 1 ring containing 6 carbon atoms, such as phenyl;

an "aryloxy" radical denotes an aryl-oxy radical with "aryl" as defined previously;

an "alkoxy" radical denotes an alkyl-oxy radical with "alkyl" as defined previously.

The composition according to the invention is preferably a composition for dyeing keratin fibres, such as the hair.

"Keratinfibres" is understood particularly to mean human keratin fibres, such as the hair, eyelashes, eyebrows and body hair, preferentially the hair, eyebrows and eyelashes, more preferentially still the hair.

Amino Silicone

The composition according to the invention comprises a) at least one amino silicone.

For the purposes of the present invention, the term "silicone" denotes any organosilicon polymer or oligomer of linear or cyclic, branched or crosslinked structure, of variable molecular weight, obtained by polymerization and/or by polycondensation of suitably functionalized silanes, and constituted essentially of a repetition of main units in which the silicon atoms are linked together via oxygen atoms (siloxane bond —Si—O—Si—), optionally substituted hydrocarbon-based radicals being directly bonded via a carbon atom to said silicon atoms.

The term "amino silicone" denotes any silicone including at least one primary, secondary or tertiary amine function or a quaternary ammonium group.

The weight-average molecular weights of these amino silicones may be measured by gel permeation chromatography (GPC) at ambient temperature (25° C.), as polystyrene equivalent. The columns used are μ styragel columns. The eluent is THF and the flow rate is 1 ml/min. 200 μl of a 0.5% by weight solution of silicone in THF are injected. Detection is performed by refractometry and UV-metry.

The amino silicone can be chosen from the silicones of formula (I) below:

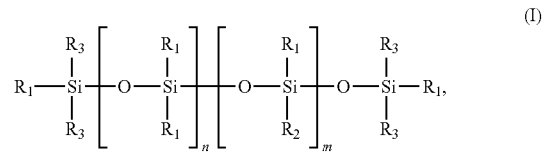

(I)

in which:

$R_1$, which may be identical or different, represents a hydrogen atom, a phenyl group, a hydroxyl group, a $C_1$-$C_8$ alkyl group, for example a methyl, or a $C_1$-$C_6$ alkoxy group, for example methoxy;

$R_2$ represents a monovalent radical of formula—$C_qH_{2q}L$ in which q is a number ranging from 2 to 8, and L is an amine group, which is optionally quaternized, chosen from the following groups:

—N(R")$_2$; —N$^+$(R")$_3$ A$^-$; —NR"-Q-N(R")$_2$ and —NR"-Q-N$^+$(R")$_3$ A$^-$, in which R", which may be identical or different, represents a hydrogen atom, a phenyl group, a benzyl group or a saturated monovalent hydrocarbon-based radical, for example a $C_1$-$C_{20}$ alkyl group; Q denotes a linear or branched group of formula $C_rH_{2r}$, r being an integer ranging from 2 to 6, preferably from 2 to 4; and A$^-$ represents a cosmetically acceptable anion, notably a halide such as fluoride, chloride, bromide or iodide;

$R_3$, which may be identical or different, represents a $C_1$-$C_8$ alkyl group, for example a methyl, or a monovalent radical of formula—$C_qH_{2q}L$ in which q is a number ranging from 2 to 8 and L is an amine group, which is optionally quaternized, chosen from the following groups:

—N(R")$_2$; —N$^+$(R")$_3$ A$^-$; —NR"-Q-N(R")$_2$ and —NR"-Q-N$^+$(R")$_3$ A$^-$, in which R", which may be identical or different, represents a hydrogen atom, a phenyl group, a benzyl group or a saturated monovalent hydrocarbon-based radical, for example a $C_1$-$C_{20}$ alkyl group; Q denotes a linear or branched group of formula $C_rH_{2r}$, r being an integer ranging from 2 to 6, preferably from 2 to 4; and A$^-$ represents a cosmetically acceptable anion, notably a halide such as fluoride, chloride, bromide or iodide; and m and n are numbers such that the sum (n+m) ranges from 1 to 2000 and in particular from 50 to 150, m possibly denoting a number from 0 to 1999 and notably from 49 to 149, and n possibly denoting a number from 1 to 2000 and notably from 1 to 10.

Preferably, $R_1$, which may be identical or different, represents a hydroxyl group or a $C_1$-$C_6$ alkoxy group for example methoxy;

$R_2$ represents a monovalent radical of formula—$C_qH_{2q}L$ in which q is a number ranging from 2 to 8 and L is an amino group chosen from the following groups:

—N(R$_4$)$_2$;

—N(R$_4$)—CH$_2$—CH$_2$—N(R$_4$)$_2$;

in which $R_4$ represents a hydrogen atom; a phenyl group; a benzyl group or a saturated monovalent hydrocarbon-based radical, for example a $C_1$-$C_{20}$ alkyl group;

$R_3$, which may be identical or different, represents a $C_1$-$C_8$ alkyl group, for example a methyl; and m and n are numbers such that the sum (n+m) ranges from 1 to 2000 and in particular from 50 to 150, m possibly denoting a number from 0 to 1999 and notably from 49 to 149, and n possibly denoting a number from 1 to 2000 and notably from 1 to 10.

According to one particular embodiment, the amino silicone(s) correspond to polysiloxanes corresponding to formula (A) below:

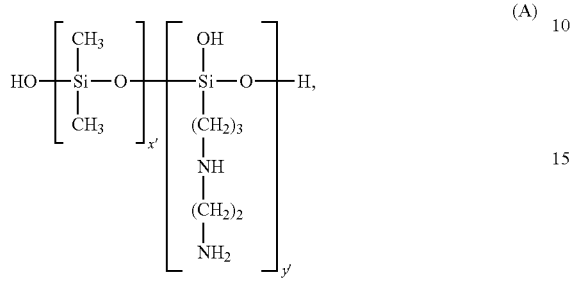
(A)

in which x' and y' are integers such that the weight-average molecular weight (Mw) is between 5000 and 500 000 approximately.

According to one preferred embodiment, the amino silicone(s) are chosen from the silicones of formula (II) below:

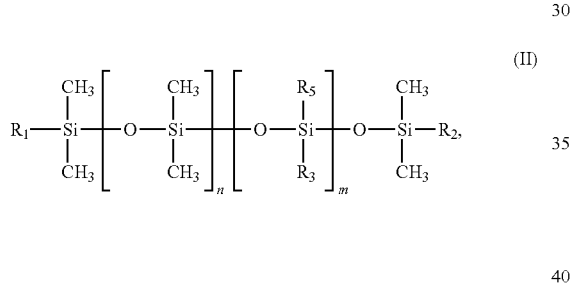
(II)

in which:
- m and n are numbers such that the sum (m+n) ranges from 1 to 1000, in particular from 50 to 350 and more particularly from 150 to 250, n possibly denoting a number from 0 to 999, in particular from 49 to 349 and more particularly from 159 to 239, and m possibly denoting a number from 1 to 1000, in particular from 1 to 50;
- $R_1$ and $R_2$, which may be identical or different, represent a $C_1$-$C_8$ alkyl group, for example a methyl, a hydroxyl group or a $C_1$ to $C_6$ and preferably $C_1$ to $C_4$ alkoxy group;
- $R_3$ represents a monovalent radical of formula —$C_qH_{2q}$L in which q is a number ranging from 2 to 8 and L is an amino group chosen from the following groups:
  —$N(R_4)_2$;
  —$N(R_4)$—$CH_2$—$CH_2$—$N(R_4)_2$;
in which $R_4$ represents a hydrogen atom; a phenyl group; a benzyl group or a saturated monovalent hydrocarbon-based radical, for example a $C_1$-$C_{20}$ alkyl group; and
- $R_5$ represents a hydroxyl group, a $C_1$-$C_8$ alkyl group, for example a methyl, or a $C_1$-$C_6$ alkoxy group, for example methoxy.

More preferentially, the amino silicone(s) are chosen from the silicones of formula (III) below:

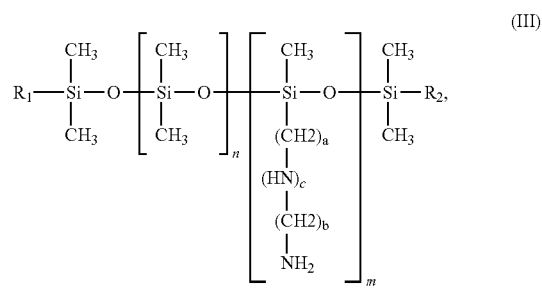
(III)

in which:
- m and n are numbers such that the sum (m+n) ranges from 1 to 1000, in particular from 50 to 350 and more particularly from 150 to 250, n possibly denoting a number from 0 to 999, in particular from 49 to 349 and more particularly from 159 to 239, and m possibly denoting a number from 1 to 1000, in particular from 1 to 50;
- $R_1$ and $R_2$, which may be identical or different, represent a $C_1$ to $C_4$ alkoxy group, and preferably a methoxy radical;
- a denotes an integer ranging from 0 to 6;
- b denotes an integer ranging from 1 to 6;
- c denotes an integer equal to 0 or 1.

Preferably $R_1$ and $R_2$ are identical.

Preferably, the amino silicone(s) are chosen:
from the silicones of formula (IV) below:

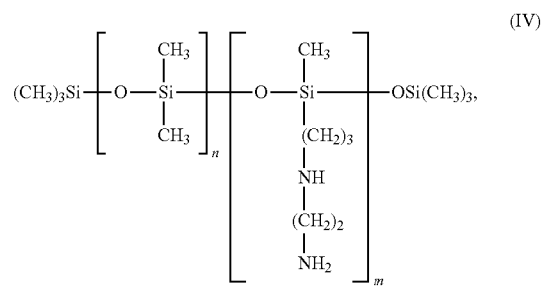
(IV)

in which m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;
from the compounds of formula (V) below:

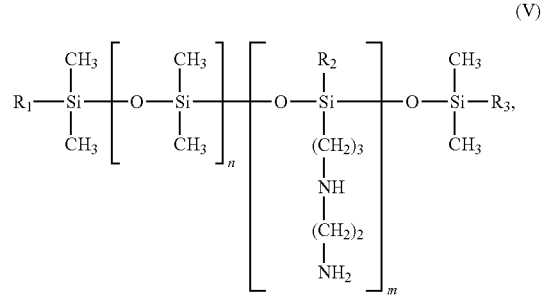
(V)

in which:

m and n are numbers such that the sum (n+m) ranges from 1 to 1000, in particular from 50 to 250 and more particularly from 100 to 200; n possibly denoting a number from 0 to 999 and notably from 49 to 249 and more particularly from 125 to 175, and m possibly denoting a number from 1 to 1000, notably from 1 to 10, more particularly from 1 to 5;

$R_1$, $R_2$ and $R_3$, which may be identical or different, represent a hydroxyl or $C_1$-$C_4$ alkoxy radical, at least one of the radicals $R_1$ to $R_3$ denoting an alkoxy radical.

The hydroxy/alkoxy mole ratio preferably ranges from 0.2:1 to 0.4:1 and preferably from 0.25:1 to 0.35:1 and more particularly is equal to 0.3:1.

The weight-average molecular weight (Mw) of these silicones of formula (V) preferably ranges from 2000 to 1 000 000 and more particularly from 3500 to 200 000.

A product containing amino silicones of structure (V) is sold by Wacker under the name Belsil® ADM 652.

from the silicones of formula (VI) below:

(VI)

[Chemical structure showing siloxane with CH3 groups, linked via O, with n and m subscripts, containing an A-NH-(CH2)2-NH2 side chain, terminated by HO-Si and Si-OH groups]

in which:

m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

A denotes a linear or branched alkylene radical having from 4 to 8 carbon atoms and preferably 4 carbon atoms. This radical is preferably linear.

The weight-average molecular weight (Mw) of these amino silicones of formula (VI) preferably ranges from 2000 to 1 000 000 and even more particularly from 3500 to 200 000.

A silicone corresponding to this formula (VI) is, for example, Xiameter MEM 8299 Emulsion from Dow Corning.

from the silicones of formula (VII) below:

(VII)

[Chemical structure showing siloxane with CH3 groups, linked via O, with n and m subscripts, containing an A-NH-(CH2)2-NH2 side chain, terminated by H3C-Si and Si-CH3 groups]

in which:

m and n are numbers such that the sum (n+m) ranges from 1 to 2000 and in particular from 50 to 150, n possibly denoting a number from 0 to 1,999 and notably from 49 to 149, and m possibly denoting a number from 1 to 2000 and notably from 1 to 10;

A denotes a linear or branched alkylene radical having from 4 to 8 carbon atoms and preferably 4 carbon atoms. This radical is preferably branched.

The weight-average molecular weight (Mw) of these amino silicones of formula (VII) preferably ranges from 500 to 1 000 000 and even more particularly from 1000 to 200000.

A silicone corresponding to this formula (VII) is, for example, DC2-8566 Amino Fluid from Dow Corning.

and mixtures thereof.

Particularly preferably, the amino silicone(s) are chosen from the silicones of formula (III).

The weight-average molecular weight (Mw) of an amino silicone of formula (III) preferably ranges from 1000 to 200 000 and even more particularly from 2000 to 100 000 and more particularly from 2000 to 50 000.

An amino silicone corresponding to formula (II) is, for example, the compound having the trade name KF 857, sold by Shin-Etsu, or the compound having the trade name KF 862, sold by Shin-Etsu.

The composition according to the invention may comprise one or more amino silicones present in a total amount ranging from 0.1% to 40% by weight, preferably from 0.5% to 30% by weight, preferentially from 1% to 20% by weight, better still from 2% to 15% by weight, even better still from 4% to 10% by weight, relative to the total weight of the composition.

Non-Amino Silicone

As indicated above, the composition according to the invention comprises at least one non-amino silicone having a weight-average molecular weight of less than or equal to 1500 g/mol.

For the purposes of the present invention, the term "non-amino silicone" denotes any silicone not comprising any primary, secondary or tertiary amine groups or quaternary ammonium groups.

Preferably, the non-amino silicone is non-cyclic.

The term "non-cyclic silicone" means a silicone which does not form a ring.

Preferably, the non-amino silicone is chosen from the silicones of formula (VIII) below:

(VIII)

[Chemical structure showing siloxane with CH3 groups, linked via O, with n and i subscripts, terminated by R2-Si and Si-R2 groups, with R1 substituent]

in which:

$R_1$ independently represents an alkyl group containing from 1 to 10 carbon atoms, preferably from 1 to 4 carbon atoms, more preferentially a methyl; or an alkoxy group containing from 1 to 2 carbon atoms;

$R_2$ independently represents a hydroxyl group or an alkoxy group containing from 1 to 2 carbon atoms;

i denotes an integer ranging from 0 to 18, n denotes an integer ranging from 0 to 18 with n+i ranging from 4 to 18.

Preferably, the non-amino silicone(s) of formula (VIII) are such that:
- $R_1$ independently represents an alkyl group containing from 1 to 10 carbon atoms, preferably from 1 to 4 carbon atoms, more preferentially a methyl;
- $R_2$ independently represents a hydroxyl group or an alkoxy group containing from 1 to 2 carbon atoms;
- i denotes an integer ranging from 0 to 18, n denotes an integer ranging from 0 to 18 with n+i ranging from 4 to 18.

More preferentially, the non-amino silicone(s) of formula (VIII) are such that:
- $R_1$ independently represents an alkyl group containing from 1 to 4 carbon atoms, more preferentially a methyl;
- $R_2$ independently represents a hydroxyl group;
- i denotes an integer ranging from 0 to 18, n denotes an integer ranging from 0 to 18 with n+i ranging from 4 to 18.

As indicated above, the non-amino silicone(s) have a weight-average molecular weight of less than or equal to 1500 g/mol.

Preferably, the non-amino silicone(s) have a weight-average molecular weight of less than or equal to 1300 g/mol.

Advantageously, the weight-average molecular weight of the non-amino silicone(s) ranges from 460 to 1500 g/mol, more preferentially from 500 to 1300 g/mol.

Preferably, the non-amino silicone(s) that may be used in the context of the invention are represented by formula (IX) below:

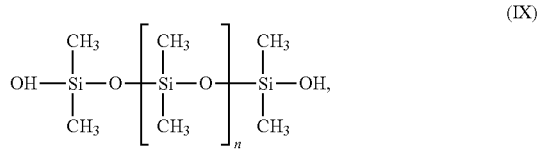

in which n denotes an integer ranging from 4 to 18.

Among the non-amino silicones, in particular those of formula (VIII), mention may be made of polydimethylsiloxanes (PDMS) bearing alkoxy end functions, such as those sold by Gelest under the reference DMS-XM11 or polydimethylsiloxanes (PDMS) bearing hydroxyl end functions, such as those sold by Sigma-Aldrich under the reference 481939 (Mn ~550).

The composition according to the invention may comprise one or more non-amino silicones present in a total amount ranging from 0.1% to 30% by weight, preferably from 0.5% to 25% by weight, more preferentially from 1% to 20% by weight, even more preferentially from 2% to 15% by weight, even better still from 2% to 6% by weight, relative to the total weight of the composition according to the invention.

Weight Ratio

Advantageously, the amino silicone/non-amino silicone weight ratio varies from 9/1 to 1/9, preferably from 5/1 to 1/5, more preferentially from 3/1 to 1/3.

Colouring Agent

As indicated above, the composition according to the invention comprises at least one colouring agent chosen from pigments, direct dyes and mixtures thereof.

Pigment

Preferably, the composition according to the invention comprises one or more pigments.

Preferably, the colouring agent(s) are chosen from pigments.

The term "pigment" is intended to mean any pigment that gives colour to keratin materials. Their solubility in water at 25° C. and at atmospheric pressure (760 mmHg) is less than 0.05% by weight, and preferably less than 0.01%.

The pigments which can be used are in particular chosen from the organic and/or inorganic pigments known in the art, in particular those which are described in the Kirk-Othmer Encyclopedia of Chemical Technology and in Ullmann's Encyclopedia of Industrial Chemistry.

They may be natural, of natural origin, or non-natural.

These pigments may be in pigment powder or paste form. They can be coated or uncoated.

The pigments can, for example, be chosen from inorganic pigments, organic pigments, lakes, special effect pigments, such as pearlescent agents or glitter, and mixtures thereof.

The pigment can be an inorganic pigment. The term "inorganic pigment" is understood to mean any pigment which satisfies the definition of Ullmann's Encyclopedia in the chapter "Pigments, Inorganic". Mention may be made, among the inorganic pigments of use in the present invention, of iron oxides, chromium oxides, manganese violet, ultramarine blue, chromium hydrate, ferric blue and titanium oxide.

The pigment can be an organic pigment. The term "organic pigment" is understood to mean any pigment which satisfies the definition of Ullmann's Encyclopedia in the chapter "Pigments, Organic".

The organic pigment may notably be chosen from nitroso, nitro, azo, xanthene, pyrene, quinoleine, quinoline, anthraquinone, triphenylmethane, fluorane, phthalocyanine, metalcomplex, isoindolinone, isoindoline, quinacridone, perinone, perylene, diketopyrrolopyrrole, indigo, thioindigo, dioxazine, triphenylmethane and quinophthalone compounds.

In particular, the white or coloured organic pigments may be chosen from carmine, carbon black, aniline black, azo yellow, quinacridone, phthalocyanine blue, the blue pigments codified in the Colour Index under the references CI 42090, 69800, 69825, 74100, 74160, the yellow pigments codified in the Colour Index under the references CI 11680, 11710, 19140, 20040, 21100, 21108, 47000, 47005, the green pigments codified in the Colour Index under the references CI 61565, 61570, 74260, the orange pigments codified in the Colour Index under the references CI 11725, 45370, 71105, the red pigments codified in the Colour Index under the references CI 12085, 12120, 12370, 12420, 12490, 14700, 15525, 15580, 15620, 15630, 15800, 15850, 15865, 15880, 26100, 45380, 45410, 58000, 73360, 73915, 75470, the pigments obtained by oxidative polymerization of indole or phenol derivatives as described in patent FR 2 679 771.

Examples that may also be mentioned include pigment pastes of organic pigments, such as the products sold by Hoechst under the names:
- Cosmenyl Yellow 10G: Yellow 3 pigment (CI 11710);
- Cosmenyl Yellow G: Yellow 1 pigment (CI 11680);
- Cosmenyl Orange GR: Orange 43 pigment (CI 71105);
- Cosmenyl Red R: Red 4 pigment (CI 12085);
- Cosmenyl Carmine FB: Red 5 pigment (CI 12490);
- Cosmenyl Violet RL: Violet 23 pigment (CI 51319);
- Cosmenyl Blue A2R: Blue 15.1 pigment (CI 74160);
- Cosmenyl Green GG: Green 7 pigment (CI 74260);
- Cosmenyl Black R: Pigment BLACK 7 (CI 77266).

The pigments in accordance with the invention can also be in the form of composite pigments, such as are described in patent EP 1 184 426. These composite pigments may be composed notably of particles including an inorganic core, at least one binder for attaching the organic pigments to the core, and at least one organic pigment which at least partially covers the core.

The organic pigment can also be a lake. The term "lake" is intended to mean dyes adsorbed onto insoluble particles, the assembly thus obtained remaining insoluble during use.

The inorganic substrates onto which the dyes are adsorbed are, for example, alumina, silica, calcium sodium borosilicate or calcium aluminium borosilicate and aluminium.

Among the dyes, mention may be made of carminic acid. Mention may also be made of the dyes known under the following names: D & C Red 21 (CI 45 380), D & C Orange 5 (CI 45 370), D & C Red 27 (CI 45 410), D & C Orange 10 (CI 45 425), D & C Red 3 (CI 45 430), D & C Red 4 (CI 15 510), D & C Red 33 (CI 17 200), D & C Yellow 5 (CI 19 140), D & C Yellow 6 (CI 15 985), D & C Green (CI 61 570), D & C Yellow 10 (CI 77 002), D & C Green 3 (CI 42 053), D & C Blue 1 (CI 42 090).

An example of a lake that may be mentioned is the product known under the following name: D&C Red 7 (CI 15 850:1).

The pigment can also be a special effect pigment. The term "special effect pigments" means pigments that generally create a coloured appearance (characterized by a certain shade, a certain vivacity and a certain level of luminance) that is non-uniform and that changes as a function of the conditions of observation (light, temperature, angles of observation, etc.). They thereby differ from coloured pigments, which afford a standard uniform opaque, semi-transparent or transparent shade.

Several types of special effect pigments exist: those with a low refractive index, such as fluorescent or photochromic pigments, and those with a higher refractive index, such as nacres, interference pigments or glitter flakes.

Examples of special effect pigments that may be mentioned include nacreous pigments such as mica covered with titanium or with bismuth oxychloride, coloured nacreous pigments such as mica covered with titanium and with iron oxides, mica covered with iron oxide, mica covered with titanium and notably with ferric blue or with chromium oxide, mica covered with titanium and with an organic pigment as defined previously, and also nacreous pigments based on bismuth oxychloride.

Nacreous pigments that may be mentioned include the nacres Cellini sold by BASF (mica-TiO$_2$-lake), Prestige sold by Eckart (mica-TiO$_2$), Prestige Bronze sold by Eckart (mica-Fe$_2$O$_3$) and Colorona sold by Merck (mica-TiO$_2$—Fe$_2$O$_3$).

Mention may also be made of the gold-coloured nacres sold notably by BASF under the name Brilliant gold 212G (Timica), Gold 222C (Cloisonne), Sparkle gold (Timica), Gold 4504 (Chromalite) and Monarch gold 233X (Cloisonne); the bronze nacres sold notably by Merck under the name Bronze fine (17384) (Colorona) and Bronze (17353) (Colorona) and by BASF under the name Super bronze (Cloisonne); the orange nacres sold notably by BASF under the name Orange 363C (Cloisonne) and Orange MCR 101 (Cosmica) and by Merck under the name Passion orange (Colorona) and Matte orange (17449) (Microna); the brown nacres sold notably by BASF under the name Nu-antique copper 340XB (Cloisonne) and Brown CL4509 (Chromalite); the nacres with a copper tint sold notably by BASF under the name Copper 340A (Timica); the nacres with a red tint sold notably by Merck under the name Sienna fine (17386) (Colorona); the nacres with a yellow tint sold notably by BASF under the name Yellow (4502) (Chromalite); the red nacres with a gold tint sold notably by BASF under the name Sunstone G012 (Gemtone); the pink nacres sold notably by BASF under the name Tan opale G005 (Gemtone); the black nacres with a gold tint sold notably by BASF under the name Nu antique bronze 240 AB (Timica), the blue nacres sold notably by Merck under the name Matte blue (17433) (Microna), the white nacres with a silvery tint sold notably by Merck under the name Xirona Silver, and the golden-green pink-orange nacres sold notably by Merck under the name Indian summer (Xirona), and mixtures thereof.

Still as examples of nacres, mention may also be made of particles including a borosilicate substrate coated with titanium oxide.

Particles comprising a glass substrate coated with titanium oxide are notably sold under the name Metashine MC1080RY by Toyal.

Finally, examples of nacres that may also be mentioned include polyethylene terephthalate glitter flakes, notably those sold by Meadowbrook Inventions under the name Silver 1P 0.004×0.004 (silver glitter flakes). It is also possible to envisage multilayer pigments based on synthetic substrates, such as alumina, silica, calcium sodium borosilicate, calcium aluminium borosilicate and aluminium.

The special effect pigments may also be chosen from reflective particles, i.e. notably from particles of which the size, structure, notably the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, highlight points that are visible to the naked eye, i.e. more luminous points that contrast with their environment, making them appear to sparkle.

The reflective particles may be selected so as not to significantly alter the colouring effect generated by the colouring agents with which they are combined, and more particularly so as to optimize this effect in terms of colour rendition. They may more particularly have a yellow, pink, red, bronze, orange, brown, gold and/or coppery colour or tint.

These particles may have varied forms and may notably be in platelet or globular form, in particular in spherical form.

The reflective particles, whatever their form, may or may not have a multilayer structure and, in the case of a multilayer structure, may have, for example, at least one layer of uniform thickness, notably of a reflective material.

When the reflective particles do not have a multilayer structure, they may be composed, for example, of metal oxides, notably titanium or iron oxides obtained synthetically.

When the reflective particles have a multilayer structure, they may include, for example, a natural or synthetic substrate, notably a synthetic substrate at least partially coated with at least one layer of a reflective material, notably of at least one metal or metallic material. The substrate may be made of one or more organic and/or inorganic materials.

More particularly, it may be chosen from glasses, ceramics, graphite, metal oxides, aluminas, silicas, silicates, notably aluminosilicates and borosilicates, and synthetic mica, and mixtures thereof, this list not being limiting.

The reflective material may include a layer of metal or of a metallic material.

Reflective particles are notably described in documents JP-A-09188830, JP-A-10158450, JP-A-10158541, JP-A-07258460 and JP-A-05017710.

Still as an example of reflective particles including a mineral substrate coated with a layer of metal, mention may also be made of particles including a silver-coated borosilicate substrate.

Particles with a silver-coated glass substrate, in the form of platelets, are sold under the name Microglass Metashine REFSX 2025 PS by Toyal. Particles with a glass substrate coated with nickel/chromium/molybdenum alloy are sold under the names Crystal Star GF 550 and GF 2525 by this same company.

Use may also be made of particles comprising a metallic substrate such as silver, aluminium, iron, chromium, nickel, molybdenum, gold, copper, zinc, tin, manganese, steel, bronze or titanium, said substrate being coated with at least one layer of at least one metal oxide such as titanium oxide, aluminium oxide, iron oxide, cerium oxide, chromium oxide or silicon oxides, and mixtures thereof.

Examples that may be mentioned include aluminium powder, bronze powder or copper powder coated with $SiO_2$ sold under the name Visionaire by Eckart.

Mention may also be made of pigments with an interference effect which are not attached to a substrate, such as liquid crystals (Helicones HC from Wacker) or interference holographic glitter flakes (Geometric Pigments or Spectra f/x from Spectratek). Special effect pigments also comprise fluorescent pigments, whether these are substances which are fluorescent in daylight or which produce an ultraviolet fluorescence, phosphorescent pigments, photochromic pigments, thermochromic pigments and quantum dots, for example sold by Quantum Dots Corporation.

The variety of the pigments that may be used in the present invention makes it possible to obtain a rich palette of colours and also specific optical effects, such as metallic effects or interference effects.

The size of the pigment used in the composition according to the present invention is generally between 10 nm and 200 µm, preferably between 20 nm and 80 µm and more preferentially between 30 nm and 50 µm.

The pigments can be dispersed in the composition by virtue of a dispersant.

The dispersant serves to protect the dispersed particles against their agglomeration or flocculation. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. In particular, esters of 12-hydroxystearic acid in particular and of $C_8$ to $C_{20}$ fatty acid and of polyols such as glycerol or diglycerol are used, such as poly(12-hydroxystearic acid) stearate with a molecular weight of approximately 750 g/mol, such as the product sold under the name Solsperse 21 000 by Avecia, polyglyceryl-2 dipolyhydroxystearate (CTFA name) sold under the reference Dehymyls PGPH by Henkel, or polyhydroxystearic acid such as the product sold under the reference Arlacel P100 by Unigema, and mixtures thereof.

As other dispersants that may be used in the compositions of the invention, mention may be made of quaternary ammonium derivatives of polycondensed fatty acids, for instance Solsperse 17 000 sold by Avecia, and polydimethylsiloxane/oxypropylene mixtures such as those sold by Dow Corning under the references DC2-5185 and DC2-5225 C.

The pigments used in the composition may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described notably in Cosmetics and Toiletries, February 1990, Vol. 105, pages 53-64, before being dispersed in the composition in accordance with the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof, anionic surfactants; lecithins; sodium, potassium, magnesium, iron, titanium, zinc or aluminium salts of fatty acids, for example aluminium stearate or laurate; metal alkoxides; polyethylene; (meth)acrylic polymers, for example polymethyl methacrylates; polymers and copolymers containing acrylate units; alkanolamines; silicone compounds, for example silicones, in particular polydimethylsiloxanes; organofluorine compounds, for example perfluoroalkyl ethers; fluorosilicone compounds.

The surface-treated pigments that are useful in the composition may also have been treated with a mixture of these compounds and/or may have undergone several surface treatments.

The surface-treated pigments that are useful in the context of the present invention may be prepared according to surface-treatment techniques that are well known to a person skilled in the art, or may be commercially available as is.

Preferably, the surface-treated pigments are coated with an organic layer.

The organic agent with which the pigments are treated can be deposited on the pigments by solvent evaporation, chemical reaction between the molecules of the surface agent or creation of a covalent bond between the surface agent and the pigments.

The surface treatment can thus be carried out, for example, by chemical reaction of a surface agent with the surface of the pigments and creation of a covalent bond between the surface agent and the pigments or the fillers. This method is described in particular in patent U.S. Pat. No. 4,578,266.

Preferably, use will be made of an organic agent covalently bonded to the pigments.

The agent for the surface treatment may represent from 0.1% to 50% by weight of the total weight of the surface-treated pigment, preferably from 0.5% to 30% by weight and even more preferentially from 1% to 20% by weight of the total weight of the surface-treated pigment.

Preferably, the surface treatments of the pigments are chosen from the following treatments:

a PEG-silicone treatment, such as the AQ surface treatment sold by LCW;

a methicone treatment, for instance the SI surface treatment sold by LCW;

a dimethicone treatment, for instance the Covasil 3.05 surface treatment sold by LCW;

a dimethicone/trimethyl siloxysilicate treatment, for instance the Covasil 4.05 surface treatment sold by LCW;

a magnesium myristate treatment, for instance the MM surface treatment sold by LCW;

an aluminium dimyristate treatment, such as the MI surface treatment sold by Miyoshi;

a perfluoropolymethylisopropyl ether treatment, such as the FHC surface treatment sold by LCW;

an isostearyl sebacate treatment, such as the HS surface treatment sold by Miyoshi;

a perfluoroalkyl phosphate treatment, for instance the PF surface treatment sold by Daito;

an acrylate/dimethicone copolymer and perfluoroalkyl phosphate treatment, for instance the FSA surface treatment sold by Daito;

a polymethylhydrosiloxane/perfluoroalkyl phosphate treatment, for instance the FS01 surface treatment sold by Daito;

an acrylate/dimethicone copolymer treatment, for instance the ASC surface treatment sold by Daito;

an isopropyl titanium triisostearate treatment, for instance the ITT surface treatment sold by Daito;

an acrylate copolymer treatment, for instance the APD surface treatment sold by Daito;

a perfluoroalkyl phosphate/isopropyl titanium triisostearate treatment, for instance the PF+ITT surface treatment sold by Daito.

According to a particular embodiment of the invention, the dispersant is present with organic or inorganic pigments in submicron-sized particulate form in the dye composition.

The term "submicron" or "submicronic" refers to pigments having a particle size that has been micronized by a micronization method and having a mean particle size of less than a micrometre (µm), in particular between 0.1 and 0.9 µm, and preferably between 0.2 and 0.6 µm.

According to one embodiment, the dispersant and the pigment(s) are present in a (dispersant:pigment) amount, according to a weight ratio, of between 1:4 and 4:1, particularly between 1.5:3.5 and 3.5:1 or better still between 1.75:3 and 3:1.

The dispersant(s) can thus have a silicone backbone, such as silicone polyether and dispersants of amino silicone type.

Among the suitable dispersants that may be mentioned are:

amino silicones, i.e. silicones comprising one or more amino groups such as those sold under the names and references: BYK LPX 21879 by BYK, GP-4, GP-6, GP-344, GP-851, GP-965, GP-967 and GP-988-1, sold by Genesee Polymers, silicone acrylates such as Tego® RC 902, Tego® RC 922, Tego® RC 1041, and Tego® RC 1043, sold by Evonik, polydimethylsiloxane (PDMS) silicones bearing carboxyl groups such as X-22162 and X-22370 by Shin-Etsu, epoxy silicones such as GP-29, GP-32, GP-502, GP-504, GP-514, GP-607, GP-682, and GP-695 by Genesee Polymers, or Tego® RC 1401, Tego® RC 1403, Tego® RC 1412 by Evonik.

According to one specific embodiment, the dispersant(s) are of amino silicone type and are cationic.

Preferably, the pigment(s) is (are) chosen from mineral, mixed mineral-organic or organic pigments.

In one variant of the invention, the pigment(s) are organic pigments, preferentially organic pigments surface-treated with an organic agent chosen from silicone compounds. In another variant of the invention, the pigment(s) are mineral pigments.

Direct Dye

The composition according to the invention can comprise one or more direct dye(s).

The term "direct dye" means natural and/or synthetic dyes, other than oxidation dyes. These are dyes that will spread superficially on the fibre.

They may be ionic or non-ionic, preferably cationic or non-ionic.

Examples of suitable direct dyes that may be mentioned include azo direct dyes; (poly)methine dyes such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures.

The direct dyes are preferably cationic direct dyes. Mention may be made of the hydrazono cationic dyes of formulae (III) and (IV) and the azo cationic dyes (V) and (VI) below:

Hét$^+$-N(Ra)-N=C(Rb)-Ar,Q-         (III),

Hét$^+$-C(Ra)=N—N(Rb)-Ar,Q         (IV),

Hét$^+$-N=N—Ar,Q-         (V)

Ar$^+$—N=N—Ar",Q-         (VI), in which formulae (III) to (VI):

Het+ represents a cationic heteroaryl radical, preferentially bearing an endocyclic cationic charge, such as imidazolium, indolium or pyridinium, which is optionally substituted, preferentially with at least one ($C_1$-$C_8$) alkyl group such as methyl;

Ar+ represents an aryl radical, such as phenyl or naphthyl, bearing an exocyclic cationic charge, preferentially ammonium, particularly tri($C_1$-$C_8$)alkylammonium, such as trimethylammonium;

Ar represents an aryl group, notably phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar" represents an optionally substituted (hetero)aryl group, such as phenyl or pyrazolyl, which are optionally substituted, preferentially with one or more ($C_1$-$C_8$)alkyl, hydroxyl, (di)($C_1$-$C_8$)(alkyl)amino, ($C_1$-$C_8$) alkoxy or phenyl groups;

Ra and Rb, which may be identical or different, represent a hydrogen atom or a ($C_1$-$C_8$)alkyl group, which is optionally substituted, preferentially with a hydroxyl group; or else the substituent Ra with a substituent of Het+ and/or Rb with a substituent of Ar form, together with the atoms that bear them, a (hetero)cycloalkyl; in particular, Ra and Rb represent a hydrogen atom or a ($C_1$-$C_4$)alkyl group optionally substituted with a hydroxyl group;

Q- represents an organic or mineral anionic counterion, such as a halide or an alkyl sulfate.

In particular, mention may be made of the azo and hydrazono direct dyes bearing an endocyclic cationic charge of formulae (III) to (VI) as defined previously. More particularly, the cationic direct dyes bearing an endocyclic cationic charge described in patent applications WO 95/15144, WO 95/01772 and EP 714 954; preferentially the following direct dyes:

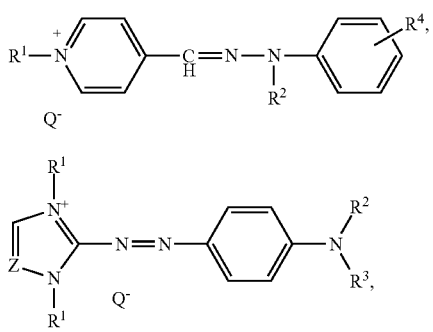

(VII)

(VIII)

in which formulae (VII) and (VIII):

$R^1$ represents a $(C_1-C_4)$alkyl group such as methyl;

$R^2$ and $R^3$, which may be identical or different, represent a hydrogen atom or a $(C_1-C_4)$alkyl group, such as methyl; and $R^4$ represents a hydrogen atom or an electron-donating group such as optionally substituted $(C_1-C_8)$alkyl, optionally substituted $(C_1-C_8)$alkoxy, or $(di)(C_1-C_8)$(alkyl)amino optionally substituted on the alkyl group(s) with a hydroxyl group; in particular, $R^4$ is a hydrogen atom;

Z represents a CH group or a nitrogen atom, preferentially CH,

Q- is an anionic counterion as defined previously, in particular a halide, such as chloride, or an alkyl sulfate, such as methyl sulfate or mesyl.

In particular, the dyes of formulae (V) and (VI) are chosen from Basic Red 51, Basic Yellow 87 and Basic Orange 31 or derivatives thereof with Q' being an anionic counterion as defined previously, particularly a halide such as chloride, or an alkyl sulfate such as methyl sulfate or mesyl.

The direct dyes may be chosen from anionic direct dyes. The anionic direct dyes of the invention are dyes commonly referred to as "acid" direct dyes owing to their affinity for alkaline substances. The term "anionic direct dye" means any direct dye including in its structure at least one $CO_2R$ or $SO_3R$ substituent with R denoting a hydrogen atom or a cation originating from a metal or an amine, or an ammonium ion. The anionic dyes may be chosen from direct nitro acid dyes, azo acid dyes, azine acid dyes, triarylmethane acid dyes, indoamine acid dyes, anthraquinone acid dyes, indigoid dyes and natural acid dyes.

As acid dyes that are useful for the invention, mention may be made of the dyes of formulae (IX), (IX'), (X), (X'), (XI), (XI'), (XII), (XII'), (XIII), (XIV), (XV) and (XVI) below:

a) the diaryl anionic azo dyes of formula (IX) or (IX'):

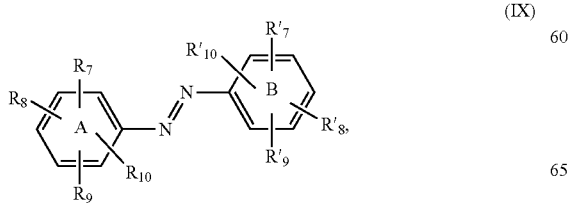

(IX)

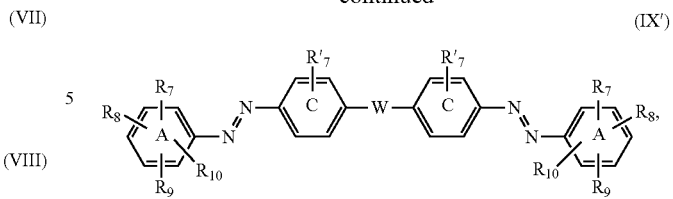

(IX')

in which formulae (IX) and (IX'):

$R_7$, $R_8$, $R_9$, $R_{10}$, $R'_7$, $R'_8$, $R'_9$ and $R'_{10}$, which may be identical or different, represent a hydrogen atom or a group chosen from:

alkyl;

alkoxy, alkylthio;

hydroxyl, mercapto;

nitro, nitroso;

$R°—C(X)—X'—$, $R°—X'—C(X)—$, $R°—X'—C(X)—X''—$ with $R°$ representing a hydrogen atom or an alkyl or aryl group; X, X' and X", which may be identical or different, representing an oxygen or sulfur atom, or NR with R representing a hydrogen atom or an alkyl group;

$(O)_2S(O^-)—$, $M^+$ with $M^+$ representing a hydrogen atom or a cationic counterion;

$(O)CO^-—$, $M^+$ with $M^+$ as defined previously;

$R''—S(O)_2—$, with $R''$ representing a hydrogen atom or an alkyl, aryl, (di)(alkyl)amino or aryl(alkyl)amino group; preferentially a phenylamino or phenyl group;

$R'''—S(O)_2—X'—$ with $R'''$ representing an optionally substituted alkyl or aryl group, X' as defined previously;

(di)(alkyl)amino;

aryl(alkyl)amino optionally substituted with one or more groups chosen from i) nitro;

ii) nitroso; iii) $(O)_2S(O^-)—$, $M^+$ and iv) alkoxy with $M^+$ as defined previously;

optionally substituted heteroaryl; preferentially a benzothiazolyl group;

cycloalkyl, notably cyclohexyl;

Ar—N=N— with Ar representing an optionally substituted aryl group; preferentially a phenyl optionally substituted with one or more alkyl, $(O)_2S(O^-)—$, $M^+$ or phenylamino groups;

or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from i) nitro; ii) nitroso; iii) $(O)_2S(O^-)—$, $M^+$; iv) hydroxyl; v) mercapto; vi) (di)(alkyl)amino; vii) $R°—C(X)—X'—$; viii) $R°—X'—C(X)—$; ix) $R°—X'—C(X)—X''—$; x) Ar—N=N— and xi) optionally substituted aryl(alkyl)amino; with $M^+$, $R°$, X, X', X" and Ar as defined previously;

W represents a sigma bond a, an oxygen or sulfur atom, or a divalent radical i) —NR— with R as defined previously, or ii) methylene —C(Ra)(Rb)- with Ra and Rb, which may be identical or different, representing a hydrogen atom or an aryl group, or alternatively Ra and Rb form, together with the carbon atom that bears them, a spiro cycloalkyl; preferentially, W represents a sulfur atom or Ra and Rb together form a cyclohexyl; it being understood that formulae (IX) and (IX') comprise at least one sulfonate radical $(O)_2S(O^-)—$, $M^+$ or one carboxylate radical $(O)CO^-—$, $M^+$ on one of the rings A, A', B, B' or C; preferentially sodium sulfonate.

As examples of dyes of formula (IX), mention may be made of: Acid Red 1, Acid Red 4, Acid Red 13, Acid Red 14, Acid Red 18, Acid Red 27, Acid Red 28, Acid Red 32, Acid Red 33, Acid Red 35, Acid Red 37, Acid Red 40, Acid Red 41, Acid Red 42, Acid Red 44, Pigment Red 57, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Yellow 6, Acid Yellow 9, Acid Yellow 36, Acid Yellow 199, Food Yellow 3, Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Food Yellow 3 or Sunset Yellow;

and, as examples of dyes of formula (IX'), mention may be made of: Acid Red 111, Acid Red 134, Acid Yellow 38;

b) the pyrazolone anionic azo dyes of formulae (X) and (X'):

(X)

(X')

in which formulae (X) and (X'):

$R_{11}$, $R_{12}$ and $R_{13}$, which may be identical or different, represent a hydrogen or halogen atom, an alkyl group or —(O)$_2$S(O$^-$), M$^+$ with M$^+$ as defined previously;

$R_{14}$ represents a hydrogen atom, an alkyl group or a group —C(O)O$^-$, M$^+$ with M$^+$ as defined previously;

$R_{15}$ represents a hydrogen atom;

$R_{16}$ represents an oxo group, in which case R'$_{16}$ is absent, or alternatively $R_{15}$ with $R_{16}$ together form a double bond;

$R_{17}$ and $R_{18}$, which may be identical or different, represent a hydrogen atom, or a group chosen from:

(O)$_2$S(O$^-$)—, M$^+$ with M$^+$ as defined previously;

Ar—O—S(O)$_2$— with Ar representing an optionally substituted aryl group; preferentially a phenyl optionally substituted with one or more alkyl groups;

$R_{19}$ and $R_{20}$ together form either a double bond, or a benzo group D', which is optionally substituted;

R'$_{16}$, R'$_{19}$ and R'$_{20}$, which may be identical or different, represent a hydrogen atom or an alkyl or hydroxyl group;

$R_{21}$ represents a hydrogen atom or an alkyl or alkoxy group;

Ra and Rb, which may be identical or different, are as defined previously; preferentially, Ra represents a hydrogen atom and Rb represents an aryl group;

Y represents either a hydroxyl group or an oxo group;

╌╌╌ represents a single bond when Y is an oxo group; and represents a double bond when Y represents a hydroxyl group;

it being understood that formulae (X) and (X') comprise at least one sulfonate radical (O)$_2$S(O$^-$)—, M$^+$ or one carboxylate radical —C(O)O$^-$, M$^+$ on one of the rings D or E; preferentially sodium sulfonate.

As examples of dyes of formula (X), mention may be made of: Acid Red 195, Acid Yellow 23, Acid Yellow 27, Acid Yellow 76, and as examples of dyes of formula (X'), mention may be made of: Acid Yellow 17;

c) the anthraquinone dyes of formulae (XI) and (XI'):

(XI)

-continued

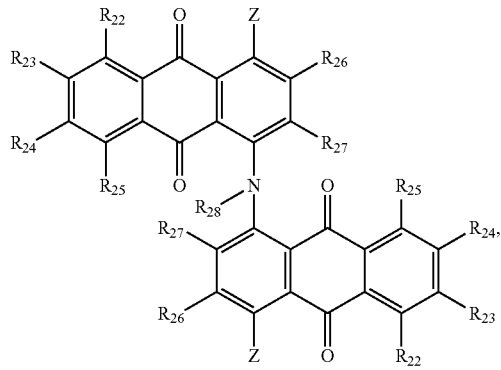

(XI')

in which formulae (XI) and (XI'):

$R_{22}$, $R_{23}$, $R_{24}$, $R_{25}$, $R_{26}$ and $R_{27}$, which may be identical or different, represent a hydrogen or halogen atom, or a group chosen from:

alkyl;

hydroxyl, mercapto;

alkoxy, alkylthio;

optionally substituted aryloxy or arylthio, preferentially substituted with one or more groups chosen from alkyl and $(O)_2S(O^-)$—, $M^+$ with $M^+$ as defined above;

aryl(alkyl)amino optionally substituted with one or more groups chosen from alkyl and $(O)_2S(O-)$—, $M^+$ with $M^+$ as defined previously;

(di)(alkyl)amino;

(di)(hydroxyalkyl)amino;

$(O)_2S(O^-)$—, $M^+$ with $M^+$ as defined above;

Z' represents a hydrogen atom or a group $NR_{28}R_{29}$ with $R_{28}$ and $R_{29}$, which may be identical or different, representing a hydrogen atom or a group chosen from:

alkyl;

polyhydroxyalkyl such as hydroxyethyl;

aryl optionally substituted with one or more groups, particularly i) alkyl such as methyl, n-dodecyl, n-butyl; ii) $(O)_2S(O^-)$—, $M^+$ with $M^+$ as defined previously; iii) $R^\circ$—C(X)—X'—, $R^\circ$—X'—C(X)—, $R^\circ$—X'—C(X)—X''— with $R^\circ$, X, X' and X'' as defined previously, preferentially $R^\circ$ represents an alkyl group;

cycloalkyl; notably cyclohexyl;

Z represents a group chosen from hydroxyl and $NR'_{28}R'_{29}$ with $R'_{28}$ and $R'_{29}$, which may be identical or different, representing the same atoms or groups as $R_{28}$ and $R_{29}$ as defined previously;

it being understood that formulae (XI) and (XI') comprise at least one sulfonate radical $(O)_2S(O^-)$—, $M^+$ or one carboxylate radical $C(O)O^-$, $M^+$; preferentially sodium sulfonate.

As examples of dyes of formula (XI), mention may be made of: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 7; EXT Violet No. 2; and, as an example of a dye of formula (XI'), mention may be made of: Acid Black 48;

d) the nitro dyes of formulae (XII) and (XII'):

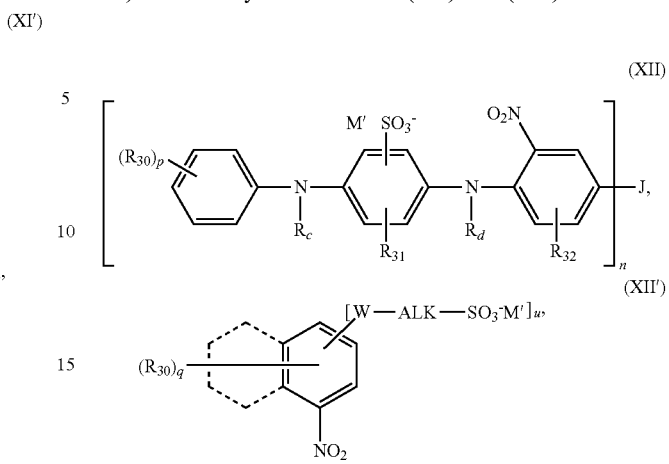

in which formulae (XII) and (XII'):

$R_{30}$, $R_{31}$ and $R_{32}$, which may be identical or different, represent a hydrogen or halogen atom, or a group chosen from:

alkyl;

alkoxy optionally substituted with one or more hydroxyl groups, alkylthio optionally substituted with one or more hydroxyl groups;

hydroxyl, mercapto;

nitro, nitroso;

polyhaloalkyl;

$R^\circ$—C(X)—X'—, $R^\circ$—X'—C(X)—, $R^\circ$—X'—C(X)—X''— with $R^\circ$, X, X' and X'' as defined previously;

$(O)_2S(O^-)$—, $M^+$ with $M^+$ as defined previously;

$(O)CO^-$—, $M^+$ with $M^+$ as defined previously;

(di)(alkyl)amino;

(di)(hydroxyalkyl)amino;

heterocycloalkyl such as piperidino, piperazino or morpholino; in particular, $R_{30}$, $R_{31}$ and $R_{32}$ represent a hydrogen atom;

Rc and Rd, which may be identical or different, represent a hydrogen atom or an alkyl group;

W is as defined previously; W particularly represents an —NH— group;

ALK represents a linear or branched divalent $C_1$-$C_6$ alkylene group; in particular, ALK represents a —$CH_2$—$CH_2$— group;

n is 1 or 2;

p represents an integer inclusively between 1 and 5;

q represents an integer inclusively between 1 and 4;

u is 0 or 1;

when n is 1, J represents a nitro or nitroso group; particularly nitro;

when n is 2, J represents an oxygen or sulfur atom, or a divalent radical —$S(O)_m$— with m representing an integer 1 or 2; preferentially, J represents an —$SO_2$— radical;

M' represents a hydrogen atom or a cationic counterion;

which may be present or absent, represents a benzo group optionally substituted with one or more groups $R_{30}$ as defined previously;

it being understood that formulae (XII) and (XII') comprise at least one sulfonate radical $(O)_2S(O^-)—$, $M^+$ or one carboxylate radical $C(O)O^-$, $M^+$; preferentially sodium sulfonate.

As examples of dyes of formula (XII), mention may be made of: Acid Brown 13 and Acid Orange 3; as examples of dyes of formula (XII'), mention may be made of: Acid Yellow 1, the sodium salt of 2,4-dinitro-1-naphthol-7-sulfonic acid, 2-piperidino-5-nitrobenzenesulfonic acid, 2-(4'—N,N-(2''-hydroxyethyl)amino-2'-nitro)anilineethanesulfonic acid, 4-β-hydroxyethylamino-3-nitrobenzenesulfonic acid; EXT D&C Yellow 7;

e) the triarylmethane dyes of formula (XIII):

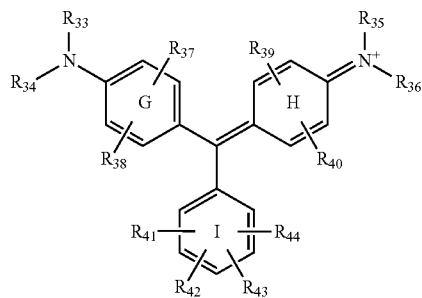

(XIII)

in which formula (XIII):
$R_{33}$, $R_{34}$, $R_{35}$ and $R_{36}$, which may be identical or different, represent a hydrogen atom or a group chosen from alkyl, optionally substituted aryl and optionally substituted arylalkyl; particularly an alkyl and benzyl group optionally substituted with a group $(O)_mS(O^-)—$, $M^+$ with $M^+$ and m as defined previously;

$R_{37}$, $R_{38}$, $R_{39}$, $R_{40}$, $R_{41}$, $R_{42}$, $R_{43}$ and $R_{44}$, which may be identical or different, represent a hydrogen atom or a group chosen from:

alkyl;
alkoxy, alkylthio;
(di)(alkyl)amino;
hydroxyl, mercapto;
nitro, nitroso;
$R°—C(X)—X'—$, $R°—X'—C(X)—$, $R°—X'—C(X)—X''—$ with $R°$ representing a hydrogen atom or an alkyl or aryl group; X, X' and X'', which may be identical or different, representing an oxygen or sulfur atom, or NR with R representing a hydrogen atom or an alkyl group;
$(O)_2S(O^-)—$, $M^+$ with $M^+$ representing a hydrogen atom or a cationic counterion;
$(O)CO^-—$, $M^+$ with $M^+$ as defined previously;
or alternatively two contiguous groups $R_{41}$ with $R_{42}$ or $R_{42}$ with $R_{43}$ or $R_{43}$ with $R_{44}$ together form a fused benzo group: I'; with I' optionally substituted with one or more groups chosen from i) nitro; ii) nitroso; iii) $(O)_2S(O^-)—$, $M^+$; iv) hydroxyl; v) mercapto; vi) (di)(alkyl)amino; vii) $R°—C(X)—X'—$; viii) $R°—X'—C(X)—$ and ix) $R°—X'—C(X)—X''—$; with $M^+$, $R°$, X, X' and X'' as defined previously;

in particular, $R_{37}$ to $R_{40}$ represent a hydrogen atom, and $R_{41}$ to $R_{44}$, which may be identical or different, represent a hydroxyl group or $(O)_2S(O^-)—$, $M^+$; and when $R_{43}$ with $R_{44}$ together form a benzo group, it is preferentially substituted with an $(O)_2S(O^-)—$ group;

it being understood that at least one of the rings G, H, I or I' comprises at least one sulfonate radical $(O)_2S(O^-)—$ or one carboxylate radical $—C(O)O$; preferentially sulfonate.

As examples of dyes of formula (XIII), mention may be made of: Acid Blue 1; Acid Blue 3; Acid Blue 7, Acid Blue 9; Acid Violet 49; Acid Green 3; Acid Green 5 and Acid Green 50.

f) the xanthene-based dyes of formula (XIV):

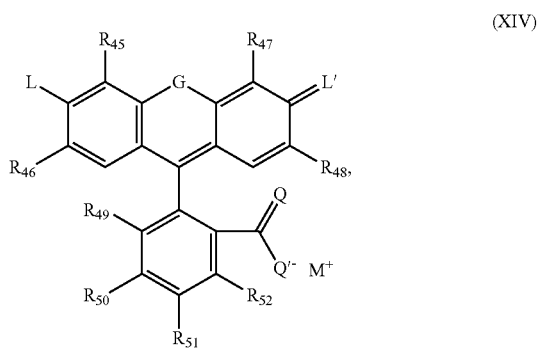

(XIV)

in which formula (XIV):

$R_{45}$, $R_{46}$, $R_{47}$ and $R_{48}$, which may be identical or different, represent a hydrogen or halogen atom;

$R_{49}$, $R_{50}$, $R_{51}$ and $R_{52}$, which may be identical or different, represent a hydrogen or halogen atom, or a group chosen from:

alkyl;
alkoxy, alkylthio;
hydroxyl, mercapto;
nitro, nitroso;
$(O)_2S(O^-)—$, $M^+$ with $M^+$ representing a hydrogen atom or a cationic counterion;
$(O)CO^-—$, $M^+$ with $M^+$ as defined previously;

particularly, $R_{49}$, $R_{50}$, $R_{51}$ and $R_{52}$ represent a hydrogen or halogen atom;

G represents an oxygen or sulfur atom or a group NRe with Re as defined previously; particularly, G represents an oxygen atom;

L represents an alkoxide O, $M^+$; a thioalkoxide S, $M^+$ or a group NRf, with Rf representing a hydrogen atom or an alkyl group, and $M^+$ as defined previously; $M^+$ is particularly sodium or potassium;

L' represents an oxygen or sulfur atom or an ammonium group: $N^+RfRg$, with Rf and Rg, which may be identical or different, representing a hydrogen atom or an optionally substituted alkyl or aryl group; L' particularly represents an oxygen atom or a phenylamino group optionally substituted with one or more alkyl or $(O)_mS(O^-)—$, $M^+$ groups with m and $M^+$ as defined previously;

Q and Q', which may be identical or different, represent an oxygen or sulfur atom; particularly, Q and Q' represent an oxygen atom;

$M^+$ is as defined previously.

As examples of dyes of formula (XIV), mention may be made of: Acid Yellow 73; Acid Red 51; Acid Red 52; Acid Red 87; Acid Red 92; Acid Red 95; Acid Violet 9;

g) the indole-based dyes of formula (XV):

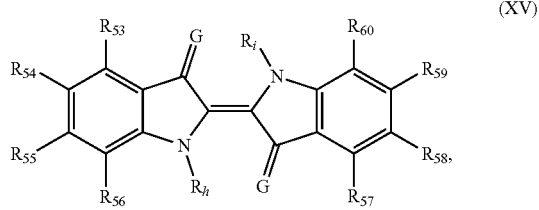

in which formula (XV):
$R_{53}$, $R_{54}$, $R_{55}$, $R_{56}$, $R_{57}$, $R_{58}$, $R_{59}$ and $R_{60}$, which may be identical or different, represent a hydrogen atom or a group chosen from:
alkyl;
alkoxy, alkylthio;
hydroxyl, mercapto;
nitro, nitroso;
$R°$—C(X)—X'—, $R°$—X'—C(X)—, $R°$—X'—C(X)—X"— with $R°$ representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, $M^+$ with $M^+$ representing a hydrogen atom or a cationic counterion;
$(O)CO^-$—, $M^+$ with $M^+$ as defined previously;
G represents an oxygen or sulfur atom or a group NRe with Re as defined previously; particularly, G represents an oxygen atom;
Ri and Rh, which may be identical or different, represent a hydrogen atom or an alkyl group;
it being understood that formula (XIII) comprises at least one sulfonate radical $(O)_2S(O^-)$—, $M^+$ or one carboxylate radical —C(O)O$^-$, $M^+$; preferentially sodium sulfonate.

As examples of dyes of formula (XV), mention may be made of: Acid Blue 74;

g) the quinoline-based dyes of formula (XVI):

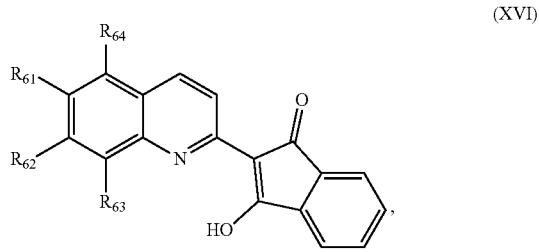

in which formula (XVI):
$R_{61}$ represents a hydrogen or halogen atom or an alkyl group;
$R_{62}$, $R_{63}$ and $R_{64}$, which may be identical or different, represent a hydrogen atom or a group $(O)_2S(O^-)$—, $M^+$ with $M^+$ representing a hydrogen atom or a cationic counterion; or alternatively $R_{61}$ with $R_{62}$, or $R_{61}$ with $R_{64}$, together form a benzo group optionally substituted with one or more groups $(O)_2S(O^-)$—, $M^+$ with $M^+$ representing a hydrogen atom or a cationic counterion;
it being understood that formula (XVI) comprises at least one sulfonate radical $(O)_2S(O^-)$—, $M^+$, preferentially sodium sulfonate.

As examples of dyes of formula (XVI), mention may be made of: Acid Yellow 2, Acid Yellow 3 and Acid Yellow 5.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Use may also be made of extracts or decoctions containing these natural dyes and notably henna-based poultices or extracts.

Preferably, the direct dyes are chosen from anionic direct dyes.

The colouring agent(s) may be present in a total content ranging from 0.001% to 20% by weight and preferably from 0.005% to 15% by weight relative to the total weight of the composition according to the invention; preferably, the colouring agent(s) are chosen from pigments.

The pigment(s) may be present in a total content ranging from 0.05% to 20% by weight, preferably from 0.1% to 15% by weight and better still from 0.5% to 10% by weight, relative to the total weight of the composition according to the invention.

The direct dye(s) may be present in a total content ranging from 0.001% to 10% by weight relative to the total weight of the composition according to the invention, preferably from 0.005% to 5% by weight relative to the total weight of the composition according to the invention.

The composition according to the invention may be an anhydrous composition.

The term "anhydrous composition" means a composition with a water content of less than 3% by weight, preferably less than 2% by weight and even more preferably less than 1% by weight relative to the total weight of the composition.

More preferentially, the composition according to the invention is free of water (zero content). The water is not added during the preparation of the composition, but may correspond to the residual water provided by the mixed ingredients.

According to another embodiment, the composition according to the invention may comprise water. Preferably, the composition can comprise from 3% to 30% by weight of water relative to the total weight of the composition.

Organic Solvents

The composition according to the invention may comprise one or more organic solvents.

As organic solvent, mention may for example be made of alkanes containing from 8 to 16 carbon atoms, and notably branched $C_8$ to $C_{16}$ alkanes such as $C_8$ to $C_{16}$ isoalkanes of petroleum origin (also called isoparaffins), such as isododecane (also called 2,2,4,4,6-pentamethylheptane), isodecane or isohexadecane.

Mention may also be made of cyclic silicones, other than the amino silicones and non-amino silicones mentioned above.

Preferably, the cyclic silicone is chosen from polydialkylsiloxanes, in particular polydimethylsiloxanes (PDMSs), and organomodified polysiloxanes comprising at least one functional group chosen from aryl groups and alkoxy groups.

Organopolysiloxanes are defined in greater detail in Walter Noll's "Chemistry and Technology of Silicones" (1968), Academic Press. They may be volatile or non-volatile.

Preferably, the cyclic silicones are volatile.

When they are volatile, the cyclic silicones can be more particularly chosen from those having a boiling point of between 60° C. and 260° C., and even more particularly from cyclic polydialkylsiloxanes containing from 3 to 7 and preferably 4 to 5 silicon atoms. These are, for example, octamethylcyclotetrasiloxane sold notably under the name Volatile Silicone© 7207 by Union Carbide or Silbione© 70045 V2 by Rhodia, decamethylcyclopentasiloxane sold under the name Volatile Silicone© 7158 by Union Carbide, and Silbione© 70045 V5 by Rhodia, and mixtures thereof.

Mention may also be made of cyclocopolymers of the dimethylsiloxane/methylalkylsiloxane type, such as Volatile Silicone© FZ 3109 sold by Union Carbide, of formula:

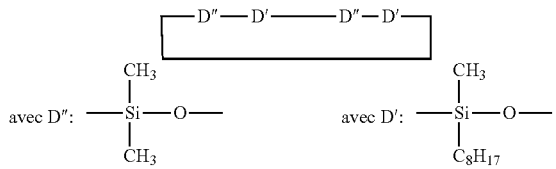

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; Advantageously, the cyclic silicones are chosen from cyclic polydialkylsiloxanes comprising from 3 to 7 and preferably from 4 to 5 silicon atoms, as mentioned above.

The organic solvents may be present in a total amount ranging from 40% to 95% by weight relative to the total weight of the composition according to the invention, preferably from 50% to 90% by weight and more preferentially from 70% to 90% by weight relative to the total weight of the composition according to the invention.

Additives

The composition according to the invention may contain any adjuvant or additive usually used.

Among the additives that may be contained in the composition according to the invention, mention may be made of reducing agents, thickeners, softeners, antifoams, moisturizers, UV-screening agents, peptizers, solubilizers, fragrances, anionic, cationic, non-ionic or amphoteric surfactants, proteins, vitamins, polymers, preserving agents, oils, waxes and mixtures thereof.

The composition according to the invention may notably be in the form of a suspension, a dispersion or a gel, in the form of a cream, a mousse, a stick, a dispersion of vesicles, notably of ionic or non-ionic lipids, a two-phase or multiphase lotion, an anhydrous liquid or an anhydrous gel.

According to one preferred embodiment, the composition according to the invention is an anhydrous liquid or an anhydrous gel.

A person skilled in the art can choose the appropriate presentation form, and also its method of preparation, on the basis of his general knowledge, taking into account on the one hand the nature of the constituents used, in particular their solubility in the support, and on the other hand the application envisaged for the composition.

According to one preferred embodiment, the composition according to the invention comprises at least one amino silicone of formula (I) as described above, at least one non-amino silicone of formula (VIII) as described above, and at least one pigment.

According to a more preferred embodiment, the composition according to the invention comprises at least one amino silicone of formula (III) as described above, at least one non-amino silicone of formula (IX), as described above, and at least one pigment.

Process

The present invention also relates to a process for the cosmetic treatment of, in particular for dyeing, keratin fibres such as the hair, in which the composition as described above is applied to said fibres.

Preferably, the composition according to the invention is a composition for dyeing keratin fibres, such as the hair.

The composition according to the invention may be used on wet or dry keratin fibres, and also on any type of fair or dark, natural or dyed, permanent-waved, bleached or relaxed fibres.

According to a particular embodiment of the process of the invention, the fibres are washed before applying the composition described above.

The application of the dye composition to the keratin fibres may be performed by any conventional means, in particular using a comb, a fine brush, a coarse brush or with the fingers.

The dyeing process, i.e. application of the dye composition to the keratin fibres, is generally carried out at ambient temperature (between 15° C. and 25° C.).

The process according to the invention may comprise a step of applying heat to the keratin fibres using a heating tool.

The heat application step of the process of the invention may be performed using a hood, a hairdryer, a straightening iron, a curling iron, a Climazon, etc.

Preferably, the heat application step of the process of the invention is performed using a hairdryer and/or a straightening iron, more preferentially using a straightening iron.

When the process of the invention involves a step of applying heat to the keratin fibres, the step of applying heat to the keratin fibres takes place after the application of the composition to the keratin fibres.

During the step of applying heat to the keratin fibres, a mechanical action may be exerted on the locks, such as combing, brushing or running the fingers through.

When the step of applying heat to the keratin fibres is performed using a hood or a hairdryer, the temperature is preferably between 30° C. and 110° C., preferentially between 50° C. and 90° C.

When the step of applying heat to the keratin fibres is performed using a straightening iron, the temperature is preferably between 110° C. and 220° C., preferably between 140° C. and 200° C.

In a particular variant, the process of the invention involves a step (b1) of applying heat using a hood, a hairdryer or a Climazon, preferably a hairdryer, and a step (b2) of applying heat using a straightening or curling iron, preferably a straightening iron.

Step (b1) may be performed before step (b2).

During step (b1), also referred to as the drying step, the fibres may be dried, for example at a temperature above or equal to 30° C. According to a particular embodiment, this temperature is above 40° C. According to a particular embodiment, this temperature is above 45° C. and below 110° C.

Preferably, if the fibres are dried, they are dried, in addition to a supply of heat, with a flow of air. This flow of air during drying makes it possible to improve the strand separation of the coating.

During drying, a mechanical action may be exerted on the locks, such as combing, brushing or running the fingers through.

During step (b2), the passage of the straightening or curling iron, preferably the straightening iron, can be carried out at a temperature ranging from 110° C. to 220° C., preferably between 140° C. and 200° C.

The present invention also relates to the use of the composition according to the invention for the cosmetic treatment of, in particular for dyeing, keratin fibres such as the hair.

The present invention will now be described more specifically by means of examples, which do not in any way limit the scope of the invention. However, the examples make it possible to support specific features, variants and preferred embodiments of the invention.

EXAMPLE

In the examples, the temperature is given in degrees Celsius and corresponds to ambient temperature (20° C.-25° C.), unless otherwise indicated, and the pressure is atmospheric pressure, unless otherwise indicated.

The following compositions are prepared (in g/100 g, AM: Active material) as described in Table 1:

TABLE 1

| Compositions | A | B | C | D | E |
|---|---|---|---|---|---|
| Amino silicone[1] | 5 | 7.5 | 2.5 | 10 | — |
| Non-amino silicone[2] | 5 | 2.5 | 7.5 | — | 10 |
| Pigment[3] | 5 | 5 | 5 | 5 | 5 |
| Solvent[4] | 85 | 85 | 85 | 85 | 85 |

[1]sold under the trade name KF862 by Shin-Etsu
[2]Polydimethylsiloxane (PDMS) (481939 sold by Sigma Aldrich)
[3]Red 7 lake (and) Isopropyl titanium triisostearate (and) Triethoxysilylethyl polydimethylsiloxyethyl dimethicone (sold by Kobo)
[4]Isododecane Thus, compositions A, B and C compositions according to the invention, while compositions D and E are comparative compositions.

Protocol for Dyeing Hair Locks

Each of compositions A to E is applied to locks of dry natural hair having 90% white hairs, in a proportion of 1 g of composition per gram of lock. The locks of hair are left for 5 minutes at ambient temperature.

At the end of the leave-on time, the lock is dried with a hairdryer (high heat and medium power) for 3 minutes. The locks are then stored at 25° C. and 40% relative humidity for 24 h.

Shampoo Washing Protocol

The locks are washed with a standard shampoo (Garnier Ultra Doux). The locks of hair are then rinsed, combed and dried with a hairdryer.

The next shampoo wash is performed on the locks obtained after the application of the hairdryer.

The protocol is repeated so that 3 shampoo washes were performed on the locks of hair.

Results

The persistence of the colour of the locks was evaluated in the CIE L*a*b* system, using a Minolta Spectrophotometer CM3600A colorimeter (illuminant D65, angle 10°, specular component included).

In this L*a*b* system, L* represents the intensity of the colour, a* indicates the green/red colour axis and b* the blue/yellow colour axis.

The persistence of the colouring is evaluated by the colour difference $\Delta E$ between the dyed locks before shampooing, then after having undergone 3 shampoo washes according to the protocol described above. The lower the $\Delta E$ value, the more persistent the colour with respect to shampoo washing. The results are given in Table 2 below.

The $\Delta E$ value is calculated according to the following equation:

$$\Delta E = \sqrt{(L^* - L_o^*)^2 + (a^* - a_o^*)^2 + (b^* - b_o^*)^2}.$$

In this equation, $L^*a^*b^*$ represent the values measured after dyeing the hair and after performing the shampoo washes, and $L_o^* a_o^* b_o^*$ represent the values measured after dyeing the hair but before shampoo washing.

TABLE 2

| Compositions | Number of shampoo washes | L* | a* | b* | $\Delta E$ |
|---|---|---|---|---|---|
| A | 0 | 31.5 | 40.7 | 16.7 | — |
|   | 3 | 46.4 | 25.6 | 9.1 | 22.6 |
| B | 0 | 31.3 | 42.1 | 16.5 | — |
|   | 3 | 44.0 | 27.5 | 8.4 | 21.0 |
| C | 0 | 32.1 | 40.6 | 14.9 | — |
|   | 3 | 54.1 | 17.6 | 5.2 | 33.3 |
| D | 0 | 31.6 | 39.9 | 15.9 | — |
|   | 3 | 51.6 | 12.6 | 4.5 | 35.8 |
| E | 0 | 32.8 | 39.3 | 14.0 | — |
|   | 3 | 57.4 | 13.4 | 6.4 | 36.5 |

As indicated above, the lower the $\Delta E$ value, the more persistent the colour with respect to shampoo washing. A difference in $\Delta E$ is significant above 2 units.

It is therefore observed that the persistence with respect to 3 shampoo washes, of compositions A, B and C, is better than that of compositions D and E.

It is therefore clearly observed that the particular combination of at least one amino silicone according to the invention and at least one non-amino silicone according to the invention exhibits a particular advantage in terms of persistence with respect to shampoo washing compared with amino silicones or non-amino silicones used alone.

Thus, the locks of hair treated with the compositions according to the invention exhibit improved colour persistence compared with the locks of hair treated with comparative compositions.

The invention claimed is:

1. A composition for treating keratin materials comprising:
   a) at least one amino silicone of formula (I) below:

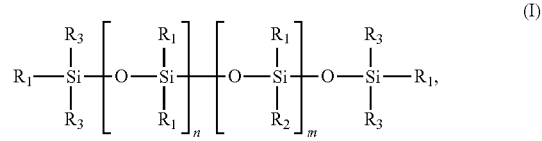

in which:
R$_1$, which may be identical or different, represents a hydrogen atom, a phenyl group, a hydroxyl group, a C$_1$-C$_8$ alkyl group, or a C$_1$-C$_6$ alkoxy group;
R$_2$ represents a monovalent radical of formula —C$_q$H$_{2q}$L in which q is a number ranging from 2 to 8 and L is an amine group, which is optionally quaternized, chosen from the following groups:
—N(R″)$_2$;
—N$^+$(R″)$_3$ A$^-$;
—NR″-Q-N(R″)$_2$; or
—NR″-Q-N$^+$(R″)$_3$ A$^-$,
in which R″, which may be identical or different, represents a hydrogen atom, a phenyl group, a benzyl group, or a saturated monovalent hydrocarbon-based radical; Q denotes a linear or branched group of formula $C_rH_{2r}$, r being an integer ranging from 2 to 6; and $A^-$ represents a cosmetically acceptable anion, which is a halide;

$R_3$, which may be identical or different, represents a $C_1$-$C_8$ alkyl group, or a monovalent radical of formula $—C_qH_{2q}L$ in which q is a number ranging from 2 to 8 and L is an amine group, which is optionally quaternized, chosen from the following groups:

—N(R")$_2$;

—N+(R")$_3$ $A^-$;

—NR"-Q-N(R")$_2$; or

—NR"-Q-N+(R")$_3$ $A^-$, in which R", which may be identical or different, represents a hydrogen atom, a phenyl group, a benzyl group, or a saturated monovalent hydrocarbon-based radical; Q denotes a linear or branched group of formula $C_rH_{2r}$, r being an integer ranging from 2 to 6; and $A^-$ represents a cosmetically acceptable anion, which is a halide; and m and n are numbers such that the sum (n+m) ranges from 1 to 2000, m denoting a number from 0 to 1999, and n denoting a number from 1 to 2000;

b) at least one non-amino silicone having a weight-average molecular weight of less than or equal to 1500 g/mol; and c) at least one coloring agent chosen from pigments, direct dyes, or mixtures thereof.

2. The composition according to claim 1, further comprising a) at least one second amino silicone of formula (II) below:

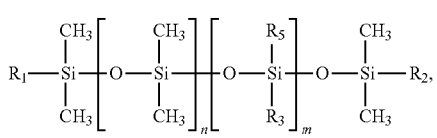

in which:

m and n are numbers such that the sum (m+n) ranges from 1 to 1000, n denoting a number from 0 to 999, and m denoting a number from 1 to 1000;

$R_1$ and $R_2$, which may be identical or different, represent a $C_1$-$C_8$ alkyl group, a hydroxyl group or a $C_1$-$C_6$ alkoxy group;

$R_3$ represents a monovalent radical of formula $—C_qH_{2q}L$ in which q is a number ranging from 2 to 8 and L is an amino group chosen from the following groups:

—N(R$_4$)$_2$; or

N(R$_4$)—CH$_2$—CH$_2$—N(R$_4$)$_2$;

in which $R_4$ represents a hydrogen atom, a phenyl group, a benzyl group, or a saturated monovalent hydrocarbon-based radical; and $R_5$ represents a hydroxyl group, a $C_1$-$C_8$ alkyl group, or a $C_1$-$C_6$ alkoxy group.

3. The composition according to claim 1, further comprising a) at least one third amino silicone of formula (III) below:

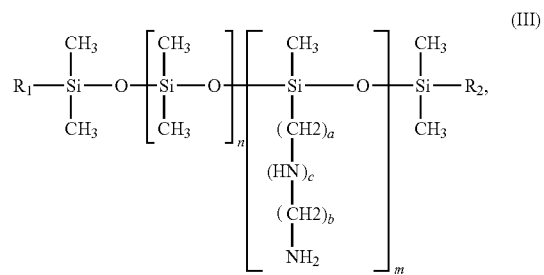

in which:

m and n are numbers such that the sum (m+n) ranges from 1 to 1000, n denoting a number from 0 to 999, and m denoting a number from 1 to 1000;

$R_1$ and $R_2$, which may be identical or different, represent a $C_1$ to $C_4$ alkoxy group;

a denotes an integer ranging from 0 to 6;

b denotes an integer ranging from 1 to 6; and c denotes an integer equal to 0 or 1.

4. The composition according to claim 1, wherein the total amount of a) amino silicones ranges from 0.1% to 40% by weight, relative to the total weight of the composition.

5. The composition according to claim 1, comprising b) at least one non-amino silicone of formula (VIII) below:

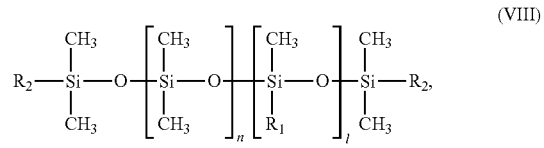

in which:

$R_1$ independently represents an alkyl group containing from 1 to 10 carbon atoms, or an alkoxy group containing from 1 to 2 carbon atoms;

$R_2$ independently represents a hydroxyl group or an alkoxy group containing from 1 to 2 carbon atoms;

i denotes an integer ranging from 0 to 18; and n denotes an integer ranging from 0 to 18, wherein n+i ranges from 4 to 18.

6. The composition according to claim 5, comprising b) at least one non-amino silicone of formula (VIII) in which:

$R_1$ independently represents an alkyl group containing from 1 to 10 carbon atoms;

$R_2$ independently represents a hydroxyl group or an alkoxy group containing from 1 to 2 carbon atoms;

i denotes an integer ranging from 0 to 18; and n denotes an integer ranging from 0 to 18, wherein n+i ranges from 4 to 18.

7. The composition according to claim 5, comprising b) at least one non-amino silicone of formula (VIII) in which:

$R_1$ independently represents an alkyl group containing from 1 to 4 carbon atoms;

$R_2$ independently represents a hydroxyl group;

i denotes an integer ranging from 0 to 18; and n denotes an integer ranging from 0 to 18, wherein n+i ranges from 4 to 18.

8. The composition according to claim 1, wherein the weight-average molecular weight of b) non-amino silicones ranges from 460 g/mol to 1500 g/mol.

9. The composition according to claim 1, wherein the total amount of b) non-amino silicones ranges from 0.1% to 30% by weight, relative to the total weight of the composition.

10. The composition according to claim 1, wherein the weight ratio of the total amount of a) amino silicones to the total amount of b) non-amino silicones ranges from 9:1 to 1:9.

11. The composition according to claim 1, wherein the total amount of c) coloring agents ranges from 0.001% to 20% by weight, relative to the total weight of the composition.

12. The composition according to claim 1 comprising at least one pigment, wherein the total amount of pigments ranges from 0.05% to 20% by weight, relative to the total weight of the composition.

13. A composition for coloring hair comprising:
a) at least one amino silicone chosen from compounds of formula (I):

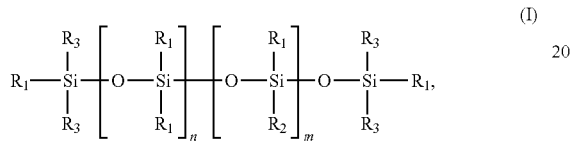

in which:
R$_1$, which may be identical or different, represents a hydrogen atom, a phenyl group, a hydroxyl group, a C$_1$-C$_8$ alkyl group, or a C$_1$-C$_6$ alkoxy group;
R$_2$ represents a monovalent radical of formula —C$_q$H$_{2q}$L in which q is a number ranging from 2 to 8 and L is an amine group, which is optionally quaternized, chosen from the following groups:
—N(R")$_2$;
—N$^+$(R")$_3$ A$^-$;
—NR"-Q-N(R")$_2$; or
—NR"-Q-N$^+$(R")$_3$ A$^-$,
in which R", which may be identical or different, represents a hydrogen atom, a phenyl group, a benzyl group, or a saturated monovalent hydrocarbon-based radical; Q denotes a linear or branched group of formula C$_r$H$_{2r}$, r being an integer ranging from 2 to 6; and A$^-$ represents a cosmetically acceptable anion, which is a halide;
R$_3$, which may be identical or different, represents a C$_1$-C$_8$ alkyl group, or a monovalent radical of formula —C$_q$H$_{2q}$L in which q is a number ranging from 2 to 8 and L is an amine group, which is optionally quaternized, chosen from the following groups:
—N(R")$_2$;
—N+(R")$_3$ A$^-$;
—NR"-Q-N(R")$_2$; or
—NR"-Q-N+(R")$_3$ A$^-$,
in which R", which may be identical or different, represents a hydrogen atom, a phenyl group, a benzyl group, or a saturated monovalent hydrocarbon-based radical; Q denotes a linear or branched group of formula C$_r$H$_{2r}$, r being an integer ranging from 2 to 6; and A$^-$ represents a cosmetically acceptable anion, which is a halide; and
m and n are numbers such that the sum (n+m) ranges from 1 to 2000, m denoting a number from 0 to 1999, and n denoting a number from 1 to 2000;
b) at least one non-amino silicone having a weight-average molecular weight ranging from 460 g/mol to 1500 g/mol, chosen from compounds of formula (VIII):

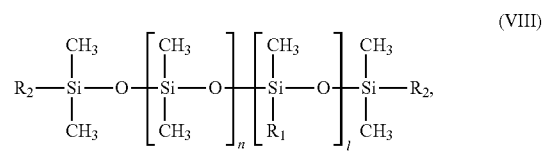

in which:
R$_1$ independently represents an alkyl group containing from 1 to 10 carbon atoms, or an alkoxy group containing from 1 to 2 carbon atoms;
R$_2$ independently represents a hydroxyl group or an alkoxy group containing from 1 to 2 carbon atoms;
i denotes an integer ranging from 0 to 18; and
n denotes an integer ranging from 0 to 18, wherein n+i ranges from 4 to 18;
c) at least one coloring agent chosen from pigments, direct dyes, or mixtures thereof; and
d) at least one organic solvent,
wherein the composition comprises a total amount of c) coloring agents sufficient to color hair, and
wherein the weight ratio of the total amount of a) amino silicones to the total amount of b) non-amino silicones ranges from 9:1 to 1:9.

14. The composition according to claim 13, wherein the total amount of a) amino silicones of formula (I) ranges from 2% to 15% by weight, relative to the total weight of the composition.

15. The composition according to claim 14, wherein the total amount of b) non-amino silicones of formula (VIII) ranges from 2% to 15% by weight, relative to the total weight of the composition.

16. The composition according to claim 15 comprising at least one pigment, wherein the total amount of pigments ranges from 0.5% to 10% by weight, relative to the total weight of the composition.

17. A method for treating keratin materials comprising applying to the keratin materials a composition comprising:
a) at least one amino silicone of formula (I) below:

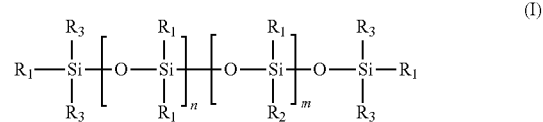

in which:
R$_1$, which may be identical or different, represents a hydrogen atom, a phenyl group, a hydroxyl group, a C$_1$-C$_8$ alkyl group, or a C$_1$-C$_6$ alkoxy group;
R$_2$ represents a monovalent radical of formula —C$_q$H$_{2q}$L in which q is a number ranging from 2 to 8 and L is an amine group, which is optionally quaternized, chosen from the following groups:
—N(R")$_2$;
—N$^+$(R")$_3$ A$^-$;
—NR"-Q-N(R")$_2$; or
—NR"-Q-N$^+$(R")$_3$ A$^-$,
in which R", which may be identical or different, represents a hydrogen atom, a phenyl group, a benzyl group, or a saturated monovalent hydrocarbon-based radical; Q denotes a linear or branched group of formula C$_r$H$_{2r}$, r being an integer ranging from 2 to 6; and A⁻ represents a cosmetically acceptable anion, which is a halide;

$R_3$, which may be identical or different, represents a $C_1$-$C_8$ alkyl group, or a monovalent radical of formula —$C_qH_{2Q}L$ in which q is a number ranging from 2 to 8 and L is an amine group, which is optionally quaternized, chosen from the following groups:

—N(R")$_2$;
—N+(R")$_3$ A⁻;
—NR"-Q-N(R")$_2$; or
—NR"-Q-N+(R")$_3$ A⁻;

in which R", which may be identical or different, represents a hydrogen atom, a phenyl group, a benzyl group, or a saturated monovalent hydrocarbon-based radical; Q denotes a linear or branched group of formula $C_rH_{2r}$, r being an integer ranging from 2 to 6; and A⁻ represents a cosmetically acceptable anion, which is a halide; and m and n are numbers such that the sum (n+m) ranges from 1 to 2000, m denoting a number from 0 to 1999, and n denoting a number from 1 to 2000;

b) at least one non-amino silicone having a weight-average molecular weight of less than or equal to 1500 g/mol; and c) at least one coloring agent chosen from pigments, direct dyes, or mixtures of two or more thereof.

18. The method according to claim 17, further comprising a step of heating the keratin materials after the composition is applied.

19. The method according to claim 17, which is a method for imparting shampoo-persistent color to the hair.

* * * * *